United States Patent
Nakamura et al.

(10) Patent No.: US 10,023,522 B2
(45) Date of Patent: Jul. 17, 2018

(54) HYDROXYALKYL ACRYLATE AND METHOD FOR PRODUCING SAME

(71) Applicant: NIPPON SHOKUBAI CO., LTD., Osaka (JP)

(72) Inventors: Masataka Nakamura, Hyogo (JP); Tokumasa Ishida, Hyogo (JP); Hiroyuki Takaki, Hyogo (JP); Hiroshi Jinno, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 14/427,108

(22) PCT Filed: Sep. 20, 2013

(86) PCT No.: PCT/JP2013/075568
§ 371 (c)(1),
(2) Date: Mar. 10, 2015

(87) PCT Pub. No.: WO2014/046261
PCT Pub. Date: Mar. 27, 2014

(65) Prior Publication Data
US 2015/0225330 A1    Aug. 13, 2015

(30) Foreign Application Priority Data
Sep. 24, 2012   (JP) ................. 2012-210108

(51) Int. Cl.
*C07C 67/26* (2006.01)
*C07C 69/54* (2006.01)

(52) U.S. Cl.
CPC .................... *C07C 67/26* (2013.01)

(58) Field of Classification Search
CPC ............... C07C 67/26; C07C 69/54
USPC ............................................. 560/209
See application file for complete search history.

(56) References Cited

U.S. PATENT DOCUMENTS

| | | | |
|---|---|---|---|
| 3,399,229 | A | 8/1968 | Kunze et al. |
| 6,380,424 | B1 | 4/2002 | Yoneda et al. |
| 2002/0040125 | A1 | 4/2002 | Matsumoto et al. |
| 2002/0082433 | A1 | 6/2002 | Agoston et al. |
| 2002/0082443 | A1* | 6/2002 | Uemura ................. C07C 67/26 560/209 |
| 2003/0229243 | A1 | 12/2003 | Ishida et al. |
| 2005/0245763 | A1* | 11/2005 | Kang ...................... C07C 51/44 562/600 |

FOREIGN PATENT DOCUMENTS

| | | |
|---|---|---|
| CN | 1502601 | 6/2004 |
| JP | 57-38747 | 3/1982 |
| JP | 2000-297062 | 10/2000 |
| JP | 2001-106654 | 4/2001 |
| JP | 2002-193885 | 7/2002 |
| JP | 2004-10602 | 1/2004 |
| JP | 2004-42015 | 2/2004 |
| JP | 2009-62289 | 3/2009 |

OTHER PUBLICATIONS

Acrylic Acid (Fischer Scientific Specification sheet for ACROS Organics 98% extra pure stabilized Acrylic acid, p. 1-4, obtained Apr. 11, 2016—hereafer referred to as ACROS).*
Carlson ("Experimental Errors and Uncertainty" downloaded from http://www.ece.rochester.edu/courses/ECE111/error_uncertainty.pdf on Jul. 24, 2017, p. 1-6).*
Chinese Office Action dated Sep. 18, 2015 in corresponding Chinese Patent Application No. 201380047873.1 (English Translation).
Notice of Reasons for Refusal dated Oct. 20, 2015 in corresponding Japanese Patent Application No. 2014-536947 (with English translation).
International Search Report dated Dec. 17, 2013 in International (PCT) Application No. PCT/JP2013/075568.
Extended European Search Report dated Apr. 21, 2016 in European Application No. 13839567.8.
Japanese Decision of Refusal dated May 31, 2016 in Japanese Patent Application No. 2014-536947 (with English translation).
Office Action dated Aug. 18, 2016 in corresponding Taiwanese Application No. 102134233, with English Translation.
Decision of Rejection dated Feb. 8, 2017 in corresponding Taiwanese Application No. 102134233, with English Translation.
Taiwanese Office Action dated Mar. 31, 2018 in corresponding Taiwanese patent application No. 102134233, with English translation.

* cited by examiner

*Primary Examiner* — Jafar Parsa
*Assistant Examiner* — Amy C Bonaparte
(74) *Attorney, Agent, or Firm* — Wenderoth, Lind & Ponack, L.L.P.

(57) ABSTRACT

The hydroxyalkyl acrylate according to the present invention is characterized in that a content amount of an ester generated from acrylic acid dimer and an alkylene oxide is not more than 0.10 mass %. The method for producing a hydroxyalkyl acrylate according to the present invention is characterized in comprising the step of reacting acrylic acid with an alkylene oxide in the presence of a catalyst, wherein a content amount of acrylic acid dimer in the raw material acrylic acid is not more than 3.00 mass %.

7 Claims, No Drawings

HYDROXYALKYL ACRYLATE AND METHOD FOR PRODUCING SAME

TECHNICAL FIELD

The present invention relates to a hydroxyalkyl acrylate which is highly stable during storage, and a method for efficiently producing a hydroxyalkyl acrylate which is highly stable during storage while it is inhibited to generate an ester as an impurity formed from acrylic acid dimer and an alkylene oxide.

BACKGROUND ART

A hydroxyalkyl (meth)acrylate such as 2-hydroxyethyl (meth)acrylate and 2-hydroxypropyl (meth)acrylate is used as a monomer for producing a poly(meth)acrylate resin. Among general (meth)acrylate monomers, a hydroxyalkyl (meth)acrylate has a characteristic of having a hydroxy group; therefore, a poly(meth)acrylate resin produced using a hydroxyalkyl (meth)acrylate as one of raw material compounds has hydroxy groups on side chains.

The above-described hydroxy group has good reactivity, since the hydroxy group is bound to a main chain through an alkylene group. Therefore, the above-described poly(meth)acrylate resin having the hydroxy groups on side chains can be crosslinked, and other functional group can be introduced thereto.

For example, the above-described poly(meth)acrylate resin having the hydroxy groups on side chains can be used as a component of a high performance paint, since scratch resistance and acid resistance are improved by a modification such as crosslinking. In addition, since high adhesion property and high hydrophilicity are exhibited by the hydroxy groups, the resin can be used as a raw material for an adhesive and contact lens and also as a processing agent for a paper or a fabric which contain cellulose.

A hydroxyalkyl (meth)acrylate is generally produced by reacting (meth)acrylic acid with an alkylene oxide in the presence of a catalyst (Patent Document 1 or the like).

When a hydroxyalkyl (meth)acrylate is industrially produced, an impurity may be generated. Therefore, a technology to inhibit such an impurity has been developed. For example, Patent Document 2 discloses a method in which a reaction is carried out while an amount of (meth)acrylic acid relative to an amount of a catalyst is adjusted in order to inhibit the generation of a dialkylene glycol mono(meth)acrylate as an impurity.

PRIOR ART DOCUMENT

Patent Document

Patent Document 1: JP 2000-297062 A
Patent Document 2: JP 2004-10602 A

DISCLOSURE OF THE INVENTION

Problems to be Solved by the Invention

As described above, a hydroxyalkyl acrylate is a compound which is important as an industrial raw material.

However, a hydroxyalkyl acrylate is a readily polymerizable compound having high reactivity. In addition, the present inventors found that an amount of an alkylene glycol diacrylate as an impurity is increased during the storage of a hydroxyalkyl acrylate. Such an alkylene glycol diacrylate has a structure in which acrylic acids are ester-bonded to each of the two hydroxy groups of an alkylene glycol, and acts as a cross-linking agent. Therefore, there is a problem that undesirable cross-linking polymerization reaction occurs and provides cause of turbidity and gelation during storage of a hydroxyalkyl acrylate.

Accordingly, the objective of the present invention is to provide a hydroxyalkyl acrylate in which an amount of an alkylene glycol diacrylate to be generated during storage is decreased and which has excellent preservation stability.

In addition, various methods have been developed as methods for producing a hydroxyalkyl acrylate while generation of an impurity is inhibited. However, acrylic acid has a problem of generation of dimer during storage. When a hydroxyalkyl acrylate is produced using raw material acrylic acid which contains such acrylic acid dimer, an ester compound may be generated from acrylic acid dimer and an alkylene oxide. However, such an ester has not been recognized as an impurity, and there has not been a method to decrease the ester.

Accordingly, the objective of the present invention is to provide a method for efficiently producing a hydroxyalkyl acrylate which has excellent preservation stability while generation of an ester formed from acrylic acid dimer and an alkylene oxide is inhibited.

Means for Solving the Problems

The present inventors studied earnestly in order to solve the above-described problems. As a result, the inventors experimentally found that the generation of an alkylene glycol diacrylate during storage of a hydroxyalkyl acrylate is caused by an ester formed from acrylic acid dimer which is mixed as an impurity with an alkylene oxide. Though the reason is not necessarily obvious, it is considered that the above-described ester is decomposed into acrylic acid and a hydroxyalkyl acrylate during storage and the acrylic acid is reacted with a hydroxyalkyl acrylate to generate an alkylene glycol diacrylate.

In addition, the present inventors found that contamination of the above ester remarkably deteriorates the quality of a hydroxyalkyl acrylate. Specifically, a hydroxyalkyl acrylate is used mainly as one of monomers for producing an acrylate resin, and the side chain hydroxy groups thereof are useful for a crosslinking reaction and a reaction to introduce functional group. When a hydroxyalkyl acrylate is contaminated with the above-described ester, for example, the ester is decomposed into one molecular of acrylic acid and one molecular of a hydroxyalkyl acrylate due to the heat of polymerization reaction, and the ratio of a hydroxyalkyl acrylate in a reaction mixture is changed. As a result, when a crosslinking reaction or a reaction to introduce functional group is carried out using the hydroxy groups, desired characteristics may possibly not be obtained. Nevertheless, when acrylic acid as a raw material for producing a hydroxyalkyl acrylate is stored, acrylic acid dimer is inescapably generated. Such a dimer is reacted with an alkylene oxide to form an ester. There is a problem that it is difficult to completely remove the ester from a hydroxyalkyl acrylate as the objective compound.

The present inventors completed the present invention by furthermore finding that an ester generated from acrylic acid dimer and an alkylene oxide is caused by acrylic acid dimer which is contained in a raw material compound, and the generation of such an ester can be remarkably inhibited by using a raw material compound in which content amount of the dimer is decreased.

Hereinafter, the present invention is described.

[1] A hydroxyalkyl acrylate, wherein a content amount of an ester generated from acrylic acid dimer and an alkylene oxide is not more than 0.10 mass %.

[2] The hydroxyalkyl acrylate according to the above [1], wherein a content amount of an alkylene glycol diacrylate is not more than 1.0 mass %.

[3] A method for producing a hydroxyalkyl acrylate, comprising the step of reacting acrylic acid with an alkylene oxide in the presence of a catalyst, wherein a content amount of acrylic acid dimer in the raw material acrylic acid is not more than 3.00 mass %.

[4] The method according to the above [3], further comprising the step of adjusting the content amount of acrylic acid dimer in the raw material acrylic acid to be not more than 3.00 mass % when the content amount is more than 3.00 mass %.

[5] The method according to the above [3] or [4], wherein a molar ratio of the alkylene oxide relative to the acrylic acid is adjusted to be not less than 1.000 and not more than 10.00, and the molar ratio is calculated by the following formula:

Molar ratio of AO/AA=(mass of AO/molecular weight of AO)/({mass of raw material AA× [(100−concentration of AA dimer)/100]}/molecular weight of AA)

wherein AO represents alkylene oxide, AA represents acrylic acid, molar ratio of AO/AA represents the molar ratio of the alkylene oxide relative to the acrylic acid, units of mass of AO and mass of AA are g, and a unit of concentration of AA dimer is mass %.

[6] The method according to any one of the above [3] to [5], wherein an initial charged amount of the raw material acrylic acid is adjusted to be not more than 90 mass % of the whole use amount, and after all of or a part of the alkylene oxide is supplied, the rest raw material acrylic acid is supplied.

[7] The method according to any one of the above [3] to [6], wherein ethylene oxide or propylene oxide is used as the alkylene oxide.

Effect of the Invention

The hydroxyalkyl acrylate according to the present invention is superior in preservation stability. Specifically, a generation amount of an alkylene glycol diacrylate during storage is decreased. Such an alkylene glycol diacrylate causes turbidity and gelation during the preservation of a hydroxyalkyl acrylate, since the alkylene glycol diacrylate acts as a crosslinking agent. The hydroxyalkyl acrylate according to the present invention is superior in preservation stability, since the content amount of an alkylene glycol diacrylate is decreased so that the above-described turbidity and gelation are inhibited.

In addition, the above-described alkylene glycol diacrylate also acts as a crosslinking agent when a hydroxyalkyl acrylate is polymerized, and causes turbidity and undesired gelation of a reaction mixture. Therefore, the hydroxyalkyl acrylate according to the present invention is of good quality as a raw material monomer.

Furthermore, according to the present invention, a hydroxyalkyl acrylate can be easily produced while the generation of an ester as an impurity formed from acrylic acid dimer and an alkylene oxide is inhibited by merely selecting an appropriate raw material compound or preliminarily adjusting a raw material compound. For example, the present inventors found that the above ester impairs preservation stability of a hydroxyalkyl acrylate. In addition, when a hydroxyalkyl acrylate which is contaminated by the ester is used as a raw material for a polyacrylate resin, desired properties may not be possibly acquired. On the other hand, the amount of the ester contained in a hydroxyalkyl acrylate as the target compound may be decreased to a certain extent by purification such as distillation; however, it is difficult to completely remove the ester when the ester is generated in relatively large amount. Therefore, the present invention is industrially very useful as a technology which relates to a high quality hydroxyalkyl acrylate.

MODE FOR CARRYING OUT THE INVENTION

The hydroxyalkyl acrylate according to the present invention is characterized in that the content amount of an ester as an impurity which is generated from acrylic acid dimer and an alkylene oxide is 0.10 mass % or less. More specifically, when a hydroxyalkyl acrylate is produced from acrylic acid and an alkylene oxide, Michael addition reaction occurs between two molecules of acrylic acids and the generated acrylic acid dimer is reacted with an alkylene oxide to generate the following ester compounds ($I^1$) and ($I^2$), which contaminate the hydroxyalkyl acrylate as an impurity. Hereinafter, the following ester compound ($I^1$) and ester compound ($I^2$) are collectively referred to as "ester compound (I)".

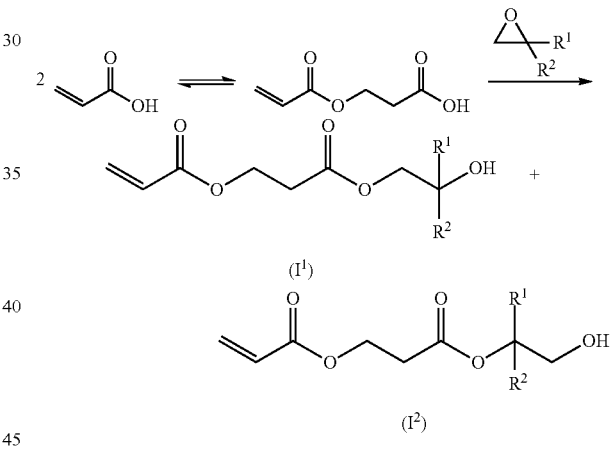

wherein $R^1$ and $R^2$ are independently represent a hydrogen atom or a $C_{1-4}$ alkyl group.

In the present invention, the term "$C_{1-4}$ alkyl group" means a straight-chain or branched-chain monovalent saturated aliphatic hydrocarbon group of which carbon atom number is not less than 1 and not more than 4. The group is exemplified by methyl, ethyl, n-propyl, isopropyl, n-butyl, isobutyl, s-butyl and t-butyl, and is preferably a $C_{1-2}$ alkyl group and more preferably methyl.

The present inventors found that when a hydroxyalkyl acrylate is contaminated by the above-described ester compound (I), an amount of an alkylene glycol diacrylate is increased over time during storage. Though the reason for the findings is not necessarily clear, there is the possibility that the ester compound (I) is decomposed into acrylic acid and a hydroxyalkyl acrylate, and the acrylic acid is reacted with a hydroxyalkyl acrylate to generate an alkylene glycol diacrylate. Accordingly, the present inventors found that preservation stability of a hydroxyalkyl acrylate can be improved by decreasing a content amount of the ester compound (I) contained in the hydroxyalkyl acrylate.

In addition, when a hydroxyalkyl acrylate which is contaminated by the ester compound (I) is subjected to a polymerization reaction as one of monomers, a dehydration polymerization reaction or a transesterification reaction occurs between the ester compound (I) and a raw material compound or a polymerization reaction product so that a desired structure of a polymer is changed. As a result, there is a problem that properties of the target polymer are affected. Such a problem can be also solved by using the hydroxyalkyl acrylate according to the present invention, of which content amount of the ester compound (I) is decreased.

Specifically, a content amount of the ester compound (I) in the hydroxyalkyl acrylate according to the present invention is not more than 0.10 mass %. If a content amount of the ester compound (I) in the hydroxyalkyl acrylate according to the present invention exceeds 0.10 mass %, preservation stability of the hydroxyalkyl acrylate may be possibly insufficient. In addition, the content amount beyond 0.10 mass % is not preferred, since the hydroxy group of the above-described ester compound (I) may be preferentially reacted or a dehydration polymerization reaction may occur between the above-described ester compound (I) and a raw material monomer or a polymer product during a polymerization reaction or a crosslinking reaction so that a polyacrylate resin having desired property may not be obtained. The content amount of the above-described ester compound (I) is preferably not more than 0.090 mass %, more preferably not more than 0.080 mass %, even more preferably not more than 0.070 mass %, and particularly preferably not more than 0.055 mass %.

On the other hand, the lower limit amount of the above-described ester compound (I) in the hydroxyalkyl acrylate according to the present invention is not limited and is ideally 0 mass %. The lower limit may be 0.0001 mass %, which is detection limit of general gas chromatography, 0.0005 mass % or 0.001 mass %. In other words, the hydroxyalkyl acrylate according to the present invention may contain not less than 0.0001 mass %, 0.0005 mass % or 0.001 mass % of the above-described ester compound (I).

The content amount of an alkylene glycol diacrylate as an impurity in the hydroxyalkyl acrylate according to the present invention is preferably not more than 1.0 mass %. The chemical structure of an alkylene glycol diacrylate is demonstrated as follows.

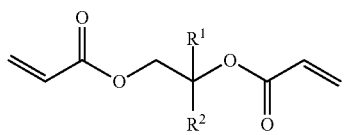

wherein $R^1$ and $R^2$ have the same meanings as the above.

Such an alkylene glycol diacrylate causes the degradation in quality of a hydroxyalkyl acrylate similarly to the above-described ester compound (I). The content amount thereof is more preferably not more than 0.8 mass %, even more preferably not more than 0.6 mass %, and particularly preferably not more than 0.5 mass %. The lower limit of the above impurity is not particularly limited, ideally 0 mass %, and preferably not less than 0.01 mass %.

Higher purity of the hydroxyalkyl acrylate according to the present invention is preferred. Specifically, the purity of the hydroxyalkyl acrylate according to the present invention is preferably not less than 95.0 mass %, more preferably not less than 96.5 mass %, and even more preferably not less than 97.5 mass %, not less than 98.5 mass % or not less than 99.5 mass %.

The hydroxyalkyl acrylate according to the present invention can be produced by sufficiently performing purification to decrease the content amount of the above-described ester compound (I) to the prescribed value. However, such a method is not suitable for, particularly, industrial mass production of a hydroxyalkyl acrylate, since yield would be decreased. Therefore, it is preferred that the hydroxyalkyl acrylate according to the present invention is produced by a method which is capable of producing the hydroxyalkyl acrylate efficiently while the generation of the above-described ester compound (I) is inhibited. As such a method, the present invention method is especially preferred.

The method for producing a hydroxyalkyl acrylate according to the present invention comprises the step of reacting acrylic acid with an alkylene oxide in the presence of a catalyst. Hereinafter, the present invention method is described step by step in order. In the present invention, acrylic acid which is used as raw material is referred to as "raw material acrylic acid" to be clearly distinguished from general acrylic acid in some cases.

In the present invention method, acrylic acid is used as one of raw material compounds. Acrylic acid serves also as a solvent during the reaction, since acrylic acid has a relatively low melting point.

In the present invention method, as acrylic acid which is used as a raw material compound, acrylic acid of which content amount of acrylic acid dimer is not more than 3.00 mass % is used. During storage of acrylic acid, acrylic acid dimer generates and the concentration thereof becomes higher with time. The present inventors found that such acrylic acid dimer reacts with an alkylene oxide to form the above-described ester compound (I) during the production of a hydroxyalkyl acrylate. The ester compound (I) has not been recognized as an impurity at all, and a cause of generation thereof has not been discussed. However, the ester compound (I) impairs the preservation stability of a hydroxyalkyl acrylate. In addition, the ester compound (I) cannot be completely separated to be removed by purification such as distillation; on the other hand, the ester compound (I) diminishes the utility value of a hydroxyalkyl acrylate as the target compound, since the ester compound (I) has a similar reactivity to a hydroxyalkyl acrylate during a polymerization reaction and is thermally decomposed. However, a hydroxyalkyl acrylate which is excellent in preservation stability can be provided by the present invention on the basis of new findings that the cause of the generation of the above-described ester compound (I) is acrylic acid dimer included in raw material acrylic acid, since contamination of the target compound by the ester compound (I) generated from acrylic acid dimer and an alkylene oxide is remarkably inhibited by using the above-described acrylic acid.

For example, the concentration of acrylic acid dimer in raw material acrylic acid means a concentration just before the raw material acrylic acid is charged into a reactor. More specifically, the concentration means a concentration within 30 minutes or less before the supply of raw material acrylic acid into a reactor is started.

A method for measuring the concentration of acrylic acid dimer in raw material acrylic acid is not particularly restricted. For example, the concentration can be measured by gas chromatography.

The concentration of acrylic acid dimer in raw material acrylic acid is more preferably not more than 2.00 mass %, even more preferably not more than 1.00 mass %, even more preferably not more than 0.80 mass %, even more preferably not more than 0.70 mass %, even more preferably not more than 0.50 mass %, and particularly preferably not more than 0.25 mass %. The lower limit thereof is not limited and is preferably 0 mass % or not more than detection limit. However, since acrylic acid dimer generates with time as described above and there is a possibility that the entire production efficiency is rather decreased if the concentration is excessively decreased, the concentration is preferably not less than 0.01 mass % and more preferably not less than 0.05 mass %.

As a method for producing the above-described raw material acrylic acid, an ordinary method can be applied. For example, when the concentration of acrylic acid dimer exceeds the desired range, the concentration can be adjusted to the desired range by appropriately mixing the raw material acrylic acid with acrylic acid of which concentration of acrylic acid dimer is low. Specifically, the concentrations of acrylic acid dimers in two or more raw material acrylic acid tanks are measured, and then raw material acrylic acid of which concentration of acrylic acid dimer exceeds the desired range is mixed with raw material acrylic acid of which concentration of acrylic acid dimer is low. As a result, it becomes possible to obtain raw material acrylic acid which contains acrylic acid dimer within the desired range. At that time, if a relation between storage temperature and generation speed of acrylic acid dimer is clarified, the step for measuring acrylic acid dimer concentration can be omitted since the concentration of acrylic acid dimer in raw material acrylic acid tank can be approximately estimated. Such mixing may be carried out in a pipe, a line mixer, a mixing tank or the like just before the obtained acrylic acid is added into a reactor, or in a storage tank. Alternatively, the concentration can be adjusted to the desired range by decomposing acrylic acid dimer using a publicly-known method.

In other words, in the present invention method, it is preferred to perform the step of adjusting the content amount of acrylic acid dimer in raw material acrylic acid to be not more than 3.00 mass %, when the content amount is more than 3.00 mass %. The concentration of dimer in acrylic acid is increased with time. For example, even if dimer concentration in raw material acrylic acid becomes higher, such acrylic acid can be positively and effectively used as a raw material of high quality hydroxyalkyl acrylate by mixing with acrylic acid having lower dimer concentration to decrease the dimer concentration.

It is preferred that temperature of raw material acrylic acid during storage is adjusted to be not more than 50° C. in order to prevent the generation of acrylic acid dimer. The temperature is more preferably not more than 40° C., even more preferably not more than 30° C., and particularly preferably not more than 20° C. On the other hand, the lower limit of the storage temperature is not particularly limited, and preferably not less than 13.5° C. since the melting point of acrylic acid is 13.5° C.

When raw material acrylic acid is charged into a storage tank or discharged from a storage tank, a long period may pass at a storage temperature or more while raw material acrylic acid remains in a transfer pipe. In such a case, when raw material acrylic acid is charged into a storage tank or discharged from a storage tank next time, raw material acrylic acid which remains in a transfer pipe may be charged into a storage tank or a reactor. As a result, a concentration of acrylic acid dimer may become possibly higher than assumed. Therefore, a stay period of raw material acrylic acid in a pipe is preferably not more than 6 months, more preferably not more than 3 months, even more preferably not more than 1 month, and particularly preferably not more than 10 days. It is more preferred that raw material acrylic acid which remains in a pipe is discharged or transferred to a storage tank by pressurizing with non-condensable gas in order to inhibit the generation of acrylic acid dimer due to staying of raw material acrylic acid in a pipe. As such noncondensable gas, air, oxygen, nitrogen and a mixture thereof may be used. Acrylic acid which is purified by a publicly-known method can be usually used as raw material acrylic acid in the present invention without additional treatment, if the acrylic acid is maintained within the above-described storage temperature range and storage period range.

The term "alkylene oxide" means ethylene oxide or a compound in which a hydrogen atom on the methylene group of ethylene oxide is substituted with an alkyl group. The number of carbon atom of the alkylene oxide is preferably not less than 2 and not more than 6, more preferably not less than 2 and not more than 4, and particularly preferably 2 or 3. In other words, ethylene oxide or propylene oxide is particularly preferred as the alkylene oxide.

The use amounts of raw material acrylic acid and an alkylene oxide may be adjusted appropriately. For example, the use amount of an alkylene oxide per mol of raw material acrylic acid is preferably not less than 1.0 mol and not more than 10 mol. When the use amount is less than 1.0 mol, the reaction between raw material acrylic acid and an alkylene oxide may possibly become difficult to proceed. On the other hand, when the use amount exceeds 10 mol, economic disadvantages may possibly be caused due to necessity of an alkylene oxide recovery step or the like. The use amount is preferably not more than 5.0 mol, more preferably not more than 3.0 mol, and particularly preferably not more than 2.0 mol.

It is known that when a hydroxyalkyl acrylate is produced, the ester compound (I) derived from acrylic acid dimer is generated as described above, and additionally an alkylene glycol diacrylate is generally generated by binding acrylic acids to two hydroxy groups of an alkylene glycol. The present inventors found that a generation amount of an alkylene glycol diacrylate can be decreased by properly adjusting a molar ratio of an alkylene oxide relative to acrylic acid which is contained in raw material acrylic acid. Such an impurity degrades the product quality of a hydroxyalkyl acrylate as the target compound similarly to the above-described ester compound (I).

It becomes possible to remarkably prevent the generation of an alkylene glycol diacrylate as an impurity by considering the concentration of acrylic acid dimer contained in raw material acrylic acid and adjusting the above-described molar ratio to the range described later. More specifically, the molar ratio of an alkylene oxide relative to acrylic acid which is contained in raw material acrylic acid is preferably adjusted to be not less than 1.000 and not more than 10.00. The molar ratio is calculated by the following formula. The molar ratio is more preferably not less than 1.010, and more preferably not more than 5.000, even more preferably not more than 2.500, even more preferably not more than 2.000, even more preferably not more than 1.500, even more preferably not more than 1.200, even more preferably not more than 1.100, even more preferably not more than 1.055. When the molar ratio is adjusted to be not more than 1.055, the generation of an alkylene glycol diacrylate can be particularly-remarkably inhibited.

Molar ratio of AO/AA=(mass of AO/molecular weight of AO)/({mass of raw material AA×[(100−concentration of AA dimer)/100]}/molecular weight of AA)

wherein AO represents alkylene oxide, AA represents acrylic acid, molar ratio of AO/AA represents the molar ratio of alkylene oxide relative to acrylic acid, units of mass of AO and mass of AA are g, and a unit of concentration of AA dimer is mass %.

The present inventors experimentally found that the generation amount of an alkylene glycol diacrylate can be decreased by adjusting the molar ratio of an alkylene oxide relative to acrylic acid to the above-described range, though the reason for the findings is not clear.

If the amount of an alkylene glycol diacrylate is increased, trouble such as occlusion of a device arises by polymerization during reaction step or distillation step of the production of a hydroxyalkyl acrylate. Hereinafter, an alkylene glycol diacrylate may be referred to as "diester" in some cases. The vapor pressure of the diester is similar to that of a hydroxyalkyl acrylate as the target compound. Therefore, when the ester generates, it is almost impossible to remove the ester. In addition, if a hydroxyalkyl acrylate which contains a lot of the diester is used as a product for homopolymerization or copolymerization with other copolymerizable monomer, turbidity may cause in the obtained polymer or undesirable gelation may cause during polymerization. Therefore, the method by which generation amount of an alkylene glycol diacrylate can be decreased is very useful for the production of a hydroxyalkyl acrylate.

In the present invention method, it is preferred to use a catalyst for accelerating the reaction of acrylic acid with an alkylene oxide. Such a catalyst is not particularly restricted, and is exemplified by a catalyst which contains at least one compound selected from the group consisting of a metal compound such as a chromium compound, an iron compound, a yttrium compound, a lanthanum compound, a cerium compound, a tungsten compound, a zirconium compound, a titanium compound, a vanadium compound, an aluminum compound and a molybdenum compound; a phosphorus compound; and an amine compound.

The metal compound which can be used for the catalyst is exemplified by a powder; a halide such as a chloride; an organic acid salt such as a formate, an acetate and an acrylate; an inorganic acid salt such as a nitrate and a sulfate; a coordination compound having a ligand such as acetylacetone; and an alkoxide such as a propoxide and a butoxide, of the above-described metal. The above phosphorus compound is exemplified by an alkylphosphine and an arylphosphine, such as trimethylphosphine and triphenylphosphine; and a quaternary phosphonium salt such as an acrylic acid salt of the phosphine.

When an amine compound is used in addition to the catalyst which contains a metal, a synergistic effect on catalytic activity is demonstrated. Specifically, a reaction conversion ratio is increased and a reaction selectivity is improved. Such an amine compound is not restricted as long as the compound has an amine functional group in the molecule, and exemplified by a trialkylamine compound; a cyclic amine compound such as pyridine; a quaternary ammonium salt thereof; and a basic anion exchange resin which contains at least one basic functional group such as a tertiary amino group, a quaternary ammonium group and a pyridinium group.

A catalyst is classified into a homogeneous catalyst, which is soluble in a reaction mixture, and a heterogeneous catalyst, which is at least partially not soluble. In the present invention, it is preferred to use a homogeneous catalyst since the reaction advances more efficiently.

The use amount of the catalyst is not particularly limited and may be adjusted appropriately. For example, in the case of a homogeneous catalyst, the use amount thereof relative to the whole use amount of acrylic acid is preferably not less than 0.001 mol % and not more than 10 mol %. When the use amount is less than 0.001 mol %, the production efficiency may be possibly decreased since a reaction rate may become too slow and a reaction time may become longer. On the other hand, when the use amount exceeds 10 mol %, a reaction selectivity of a by-product may possibly become high. The use amount is more preferably not less than 0.005 mol %, even more preferably not less than 0.01 mol %, and more preferably not more than 5 mol %, even more preferably not more than 3 mol %. In the case of a heterogeneous catalyst, the use amount relative to the whole use amount of acrylic acid is preferably not less than 5 mass % and preferably not more than 80 mass %, and more preferably not less than 10 mass % and more preferably not more than 70 mass %, for the same reason as that described for a homogeneous catalyst.

In the present invention method, a polymerization inhibitor is preferably used to inhibit polymerization of acrylic acid and a hydroxyalkyl acrylate as the target compound. Such a polymerization inhibitor is not particularly restricted, and any one which is commonly used for the production of acrylic acid or derivative thereof may be used. For example, the polymerization inhibitor to be used is exemplified by a phenol compound such as hydroquinone and p-methoxyphenol; a paraphenylenediamine such as N-isopropyl-N′-phenyl-p-phenylenediamine; a phenylamine compound such as phenothiazine; a copper dialkyldithiocarbamate such as copper dibutyldithiocarbamate, copper diethyldithiocarbamate and copper dimethyldithiocarbamate; a N-oxyl compound such as 2,2,4,4-tetramethylpiperidine-1-oxyl. In addition, a gas which contains molecular oxygen may also be used. As such a gas, air, oxygen itself, a mixed gas of oxygen and an inert gas, or the like may be used. In the case of using a gas containing molecular oxygen, the gas is preferably blown into the reaction mixture to be bubbled. Such a polymerization inhibitor may be used individually, and alternatively two or more may be used in combination.

The use amount of a polymerization inhibitor may be adjusted appropriately. For example, the use amount relative to the whole use amount of acrylic acid is preferably not less than 0.0001 mass % and not more than 1 mass %, and more preferably not less than 0.001 mass % and not more than 0.5 mass %.

A solvent may be used in the present invention method. Such a solvent may be chosen appropriately and is not particularly restricted. For example, an aliphatic hydrocarbon such as hexane; an aromatic hydrocarbon such as benzene and toluene may be used.

In the present invention method, acrylic acid is reacted with an alkylene oxide in the presence of a catalyst. If necessary, other compound may be used for the purpose such as promotion and stabilization of the reaction. The whole use amount of the raw material compounds may be used to be reacted all at once from the beginning of the reaction, or alternatively only a part of the compounds may be used at the beginning of the reaction.

For example, in general, the whole use amount of a homogeneous catalyst is preliminarily added into a reactor before the beginning of the reaction. However, the initial charged amount may be a part of the whole use amount as long as the catalytic activity can be exerted, for example, the above-described preferable ratio relative to acrylic acid can be satisfied. In such a case, the rest part may be added at the middle of the reaction. A homogeneous catalyst may be preliminarily dissolved in raw material acrylic acid or an alkylene oxide and added into a reactor. For example, a homogeneous catalyst may be dissolved in raw material acrylic acid in a dissolving vessel other than a reactor, and then supplied into the reactor together with the raw material acrylic acid.

With respect to a heterogeneous catalyst, similarly, the whole use amount thereof may be used from the beginning of the reaction, or only a part of the whole use amount may be added into a reactor at the beginning of the reaction and the rest part may be added little by little.

A polymerization inhibitor is used for preventing polymerization of acrylic acid or a hydroxyalkyl acrylate as the target compound. Therefore, the whole use amount of a polymerization inhibitor may be added into a reactor before the beginning of the reaction, or alternatively, a polymerization inhibitor may be added little by little with adding raw material acrylic acid or the like.

During the reaction, an impurity such as an alkylene glycol diacrylate may be generated as a by-product. A diester generation inhibitor may be added to prevent the generation of such a diester. The whole use amount of the diester generation inhibitor may be used from the beginning of the reaction, or properly divided to be added if necessary. The diester generation inhibitor is exemplified by one or not less than two compounds selected from the group of a carboxylic acid and an anhydride thereof, such as oxalic acid, oxalic anhydride, malonic acid, succinic acid, succinic anhydride, fumaric acid, maleic acid, maleic anhydride, salicylic acid, octanoic acid, adipic acid, sebacic acid, tetradecanedioic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, ortho-toluic acid, meta-toluic acid, para-toluic acid, phthalic acid, phthalic anhydride, isophthalic acid, terephthalic acid, 2,6-naphthalenedicarboxylic acid, pyromellitic acid, pyromellitic anhydride, trimellitic acid, trimellitic anhydride, 1,2,4-benzenetricarboxylic acid, 1,4,5,8-naphthalenetetracarboxylic acid, 1,3,5,7-naphthalenetetracarboxylic acid, and polyacrylic acid; a polyalcohol such as glycerin, diethylene glycol, trimethylolpropane, cresol, 1,2,6-hexanetriol, pentaerythritol, dipentaerythritol, 2,3,4,5-tetrahydroxyhexane, xylitol, mannitol, catechol, resorcin, 2,6-dihydroxytoluene, tert-butylcatechol, pyrogallol, 2,4-bis(hydroxymethyl)phenol, 1,2,4-trihydroxybenzene, 1,3,5-trihydroxybenzene, 2,4,6-tris(hydroxymethyl) phenol and 1,2,4,5-tetrahydroxybenzene; a metal chelator such as ethylenediaminetetraacetate, ethylenediaminetetrapropionate, nitrilotriacetate, iminodiacetate, 1,2-diaminocyclohexanetetraacetate, acetylacetone, cupferron, oxine, benzidine and diethyldithiocarbamate. The diester generation inhibitor can be also used in later distillation step.

The whole use amount of raw material acrylic acid may be used from the beginning of the reaction. However, it is preferred to supply a part of the whole use amount into a reactor at the beginning of the reaction, and after the beginning of the reaction, the rest part is added little by little. According to the findings of the present inventors, the generation of the above-described ester (I) and an alkylene glycol diacrylate as impurities can be further inhibited in the case of using raw material acrylic acid little by little more efficiently than the case of using the whole use amount of raw material acrylic acid from the beginning of the reaction.

For example, it is preferred that the initial charged amount of raw material acrylic acid is adjusted to be not more than 90 mass % of the whole use amount, and after all of or a part of an alkylene oxide is supplied to start the reaction, the rest raw material acrylic acid is added. More specifically, it is preferred that not more than 90 mass % of the whole use amount of raw material acrylic acid is added at the beginning of the reaction to be once reacted with an alkylene oxide, and then the rest part may be added all at once or in not less than two portions. The initial charged amount is more preferably not more than 50 mass %, even more preferably not more than 40% mass %, and particularly preferably not more than 35 mass %. The lower limit of the amount is not particularly limited, and is preferably not less than 1 mass % since when the amount is too small, the number of addition is increased so that the production efficiency may be possibly lowered. The amount is more preferably not less than 2 mass %, and particularly preferably not less than 5 mass %. The addition of a raw material compound in two or more portions in such a manner is referred to as sequential addition. Raw material acrylic acid may be added continuously at a constant rate or non-constant rate. Alternatively, a part of raw material acrylic acid may be added at once, and the rest part is added continuously. In the case that raw material acrylic acid is added continuously at least at the beginning of the reaction, the requirement "an initial charged amount of raw material acrylic acid is adjusted to be not more than 90 mass % of the whole use amount" can be satisfied when the amount of raw material acrylic acid at the time that the reaction starts by raising the temperature of the reaction mixture is not more than 90 mass % of the whole use amount. In the present invention, an initial charged amount means an amount of a raw material compound which exists in a reactor at the beginning of the reaction. The beginning of the reaction is described later.

In the present invention method, the generation of the ester compound (I), which is a reaction product of acrylic acid dimer as an impurity with an alkylene oxide, is inhibited by reducing the content of the dimer in raw material acrylic acid. In addition, the present inventors experimentally found that the generation amount of an alkylene glycol diacrylate in addition to the above-described ester (I) can be decreased more effectively when apart of the whole use amount of raw material acrylic acid is added into a reactor at the beginning of the reaction and the rest part is further added little by little than the case of using all of the whole use amount at once from the beginning of the reaction, though the reason is not necessarily clear. It is considered to be one reason for the experimental result that the generation of the impurities is possibly promoted by acrylic acid. Therefore, the generation of the impurities can be inhibited more effectively by reducing the apparent amount of the acid contained in the reaction mixture in the above-described manner.

When a part of the whole use amount of an alkylene oxide is added into a reactor together with an initial charged amount of raw material acrylic acid at the beginning of the reaction to be reacted, it is preferred to add the rest raw material acrylic acid and the rest alkylene oxide at not less than 0.01 hours and not more than 5 hours after the beginning of the reaction. When the period is outside the above range, a dialkylene glycol monoacrylate, which is an addition product of two molecules of alkylene oxide, may be formed as a by-product and thereby distillation yield or purity may be possibly decreased. The period from the beginning of the reaction is more preferably not less than 0.1 hours and not more than 4 hours, even more preferably not more than 3 hours, even more preferably not more than 2 hours, and particularly preferably not more than 1 hour.

The rest raw material acrylic acid and alkylene oxide are preferably added over not less than 0.1 hours and not more than 5 hours. When the addition time is less than 0.1 hours, the amount of reaction heat generated per unit time becomes large. As a result, economic disadvantages may be possibly caused. For example, a heat exchanger for cooling is required to be enlarged. When the addition time exceeds 5 hours, production efficiency may be possibly lowered. The addition time is more preferably not more than 4 hours and even more preferably not more than 3 hours.

The order for adding acrylic acid, an alkylene oxide, a catalyst, a polymerization inhibitor and others as raw material compounds is not particularly restricted, and for example, it is preferred that ethylene oxide is dissolved in raw material acrylic acid to be added since the boiling point of ethylene oxide is 10.7° C. and ethylene oxide is generally in a gaseous state at room temperature. For example, it is preferred to add an alkylene oxide into a mixture of at least a part of the whole use amount of a catalyst, a polymerization inhibitor and raw material acrylic acid.

The whole use amount of an alkylene oxide may be supplied all at once. However, it is preferred to add an alkylene oxide sequentially or continuously, and it is more preferred to add an alkylene oxide continuously, since combustion may possibly occur when a large amount of unreacted alkylene oxide exists.

The reaction can be started by bringing the temperature of a mixture containing at least a part of the whole use amount of raw material acrylic acid and an alkylene oxide up to not less than 40° C. More specifically, the mixture may be heated to not less than 40° C., or alternatively, a mixture containing at least a part of the whole use amount of raw material acrylic acid may be heated to not less than 40° C. and then, an alkylene oxide may be added thereto.

The reaction temperature is usually adjusted to be not less than 40° C. and not more than 120° C. When the reaction temperature is less than 40° C., a gas concentration of unreacted alkylene oxide in a gas phase may become high due to an excessively low reaction rate and therefore an explosion may possibly occur. As a result, a complicated operation may be required in order to secure safety. For example, it is required to reduce the gas concentration of an alkylene oxide in a gas phase by diluting the gas phase with an inert gas. In such a case, a preset pressure of a reactor is required to be higher so that economic disadvantages may possibly be caused. Alternatively, a concentration of unreacted alkylene oxide may be decreased by lowering a rate of supplying an alkylene oxide, but as a result, a longer reaction time may be required and therefore the production efficiency may be possibly lowered. On the other hand, when the reaction temperature exceeds 120° C., it may possibly become difficult to prevent the generation of the above-described ester compound (I) and an alkylene glycol diacrylate as impurities. The reaction temperature is more preferably not less than 50° C., even more preferably not less than 60° C., and even more preferably not less than 70° C., and more preferably not more than 110° C., and even more preferably not more than 100° C.

The reaction time may also be adjusted appropriately. For example, the whole use amount of raw material compounds are all added to a reactor and then the reaction is carried out for a period of not less than 30 minutes and not more than 10 hours. When raw material acrylic acid and the like are sequentially added into a reactor, raw material compounds may be reacted for a period of not less than 30 minutes and not more than 10 hours after the whole use amount of the compounds are added into a reactor.

After all of the whole use amount of the raw material compounds are added into a reactor, a reaction temperature may be raised in order to shorten a reaction period. For example, it is preferred to raise a reaction temperature by not less than 1° C. and not more than 30° C. higher than the temperature at the addition of acrylic acid and an alkylene oxide. If the increase of the temperature exceeds 30° C., a catalyst activity may be possibly decreased after the reaction. The increase of the temperature is preferably not less than 5° C. and not more than 20° C.

A pressure within a reactor during the reaction may be adjusted depending on the kinds and the use proportions of the raw material compounds to be used, and in general the reaction is preferably carried out under an increased pressure. However, there is some danger that a combustion range is enlarged in connection with such increase of reaction pressure. Although the reaction varies depending on an initial charged amount of the raw material compounds, an initial pressure, a pressure increase due to compression of the gas phase within a reactor caused by the addition of the raw material compounds after the beginning of the reaction, and the partial pressure of unreacted alkylene oxide. For example, the pressure in gauge pressure is preferably not less than 0.01 MPa and not more than 1.5 MPa, and more preferably not less than 0.05 MPa and not more than 1.0 MPa.

The reaction may be stopped when an amount of acrylic acid which remains in the reaction mixture is measured and the measured amount becomes not more than the prescribed value relative to the whole use amount. The prescribed amount is preferably not more than 0.2 mass %, and more preferably not more than 0.1 mass %. The reaction can be stopped by cooling the reaction mixture down to less than 40° C.

A method for measuring the concentration of acrylic acid which remains in the reaction mixture is not particularly restricted. The concentration is preferably measured by gas chromatography, liquid chromatography, neutralization titration and the like, and more preferably measured by neutralization titration since the concentration can be promptly measured within 10 minutes. As neutralization titration, general acid-base titration can be applied. The concentration measured by acid-base titration corresponds to a total concentration of other acidic impurity which can be titrated by alkali in addition to raw material acrylic acid which remains in the reaction mixture; however, an amount of acidic impurity is much smaller than that of acrylic acid in the reaction mixture. Therefore, it is assumed in the present invention that the concentration of acrylic acid which is contained in the reaction mixture can be measured by acid-base titration on the assumption that all of the acidic components in the reaction mixture are acrylic acid.

After the reaction is stopped, a method for collecting a hydroxyalkyl acrylate as the target compound is not restricted, and for example, the hydroxyalkyl acrylate can be collected by distillation from the reaction mixture. Specifically, a distillation method using a general distillation column, a fractionating column such as a packed column, a bubble column and a perforated plate column, or the like may be employed. The above-described method is not restrictive. When distillation is carried out for purification, other purification devices such as a rotary thin layer type evaporator may also be used in combination. The condition of distillation for purification may be adjusted appropriately, and for example, an absolute pressure may be adjusted to be not less than 1 hPa and not more than 50 hPa, temperature may be adjusted to be not less than 50° C. and not more than 120° C., and distillation period may be adjusted to be not less than 0.5 hours and not more than 24 hours. The absolute pressure is preferably not more than 20 hPa, and more preferably not more than 10 hPa. The distillation temperature is preferably not less than 60° C. and not more than 100° C. The distillation period is preferably not less than 1 hour, and preferably not more than 12 hours, more preferably not more than 6 hours, and even more preferably not more than 3 hours.

Gas bubbling may be carried out during distillation in order to prevent bumping. The amount of such gas bubbling is not particularly limited, and it is preferred to adjust the amount depending on various conditions since, for example, a too large amount of gas bubbling may become a load during distillation under a high vacuum condition. For example, the amount of gas supplied for bubbling is preferably not more than 10 vol % and not less than 0.1 vol %, relative to an evaporated volume.

An attempt to distill all of generated hydroxyalkyl acrylate may result in an increased possibility of impurity contamination. Therefore, in the case of a hydroxyalkyl acrylate, distillation is preferably stopped when not more than 95% of the generated hydroxyalkyl acrylate relative to the reaction mixture subjected to distillation is distilled. The ratio is referred to as distillate ratio in some cases. The distillate ratio in the case of a hydroxyalkyl acrylate is more preferably not more than 92%. The lower limit of the distillate ratio is not particularly limited, and is preferably not less than 80 mass %, more preferably not less than 85%, and particularly preferably not less than 88%, since productivity may be possibly lowered when the ratio is excessively low.

In the residue resulting from distillation of a hydroxyalkyl acrylate as the target compound, a catalyst is contained and a polymerization inhibitor remains in some cases. In the present invention, it is preferred that the above-described reaction is repeated two or more times, and the residual catalyst and polymerization inhibitor are used in the next and succeeding reaction as the whole or a part of a catalyst and a polymerization inhibitor. By such an embodiment, the production cost can be reduced by decreasing the use amount of a catalyst and the like, and water derived from a raw material compound can be prevented from being newly brought in.

The residue which remains after distilling off a hydroxyalkyl acrylate is usually a liquid. However, it is concerned that liquid properties of the residue may be deteriorated due to thermal history. For example, viscosity of the residue and the amount of a by-product may be increased. Therefore, the temperature of the residue is preferably maintained at not more than the distillation temperature, and when the residue is stored for a long period of time such as five days or more, the temperature is preferably maintained at not more than 50° C. The polymerization inhibitor used in the reaction works effectively also during the distillation.

According to the present invention method described above, a hydroxyalkyl acrylate as the target compound can be efficiently produced while the generation of the ester compound (I) formed from acrylic acid dimer and an alkylene oxide is inhibited. In other words, a content amount of the above-described ester (I) as an impurity is decreased in the hydroxyalkyl acrylate which is produced by the present invention method. The above-described ester (I) impairs the preservation stability of a hydroxyalkyl acrylate. Therefore, the hydroxyalkyl acrylate obtained by the present invention method is excellent in preservation stability. In addition, when the hydroxyalkyl acrylate obtained by the present invention method is used as one of the monomers for producing an acrylate resin and the side chain hydroxy group of the acrylate resin is utilized for crosslinking or introduction of a functional group, a side reaction can be inhibited.

The present application claims the benefit of the priority date of Japanese patent application No. 2012-210108 filed on Sep. 24, 2012, and all of the contents of the Japanese patent application No. 2012-210108 filed on Sep. 24, 2012 are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Unless otherwise noted, "%" means "mass %". In the present invention, "distillate ratio" means a ratio by mass of a distillate amount relative to a mass of an original reaction mixture when a certain component such as the target compound is separated by purification such as distillation.

A measurement condition of gas chromatography is shown as follows.

(1) Measurement condition of acrylic acid dimer in raw material acrylic acid

Gas chromatograph: GC-17A, manufactured by Shimadzu Corporation

Column: DB-WAX (inside diameter: 0.25 mm, length: 60 m), manufactured by J&W SCIENTIFIC Injection temperature: 250° C.

(2) Measurement condition of an ester generated from acrylic acid dimer and an alkylene oxide, and an alkylene glycol diacrylate in a hydroxyalkyl acrylate Gas chromatograph: GC-17A, manufactured by Shimadzu Corporation Column: DB-1701 (inside diameter: 0.53 mm, length: 30 m), manufactured by J&W SCIENTIFIC Injection temperature: 250° C.

Example 1: Production of Hydroxyethyl Acrylate (1) Analysis of Raw Material Acrylic Acid The acrylic acid which had been produced in the factory of the applicant of this application and stored in a tank was analyzed by gas chromatography. As a result, a concentration of acrylic acid dimer was 0.10 mass %.

(2) Esterification Reaction

The above raw material acrylic acid (658 g) produced by NIPPON SHOKUBAI CO., LTD., chromium acetate as a catalyst (2.62 g) and hydroquinone monomethyl ether as a polymerization inhibitor (1.44 g) were added into an autoclave of which capacity was 1.5 L, which was equipped with an agitator and which was made of SUS-316. After the gas phase in the autoclave was replaced by nitrogen gas, the temperature of the mixture was raised to 50° C. and the internal pressure was increased to 0.1 MPa in gauge pressure. Then, while the temperature of the mixture was maintained at 50° C., ethylene oxide (287.0 g out of 430.0 g, molar ratio relative to the pure acrylic acid was 1.070) produced by NIPPON SHOKUBAI CO., LTD. was added over about 60 minutes. Then, 143.0 g of ethylene oxide was added over about 120 minutes by changing the addition speed. After the addition of ethylene oxide, the reaction temperature was raised to 70° C. The reaction was carried out while a sample was taken with time and a concentration of unreacted acrylic acid was measured. When 3 hours passed after ethylene oxide was completely added and the concentration of unreacted acrylic acid in the whole reaction mixture became 0.10 mass %, the reaction was stopped by cooling the reaction mixture to 40° C.

The obtained reaction mixture was analyzed by gas chromatography. As a result, a concentration of ethylene glycol diacrylate was 0.20 mass %, and a concentration of an addition reaction product of acrylic acid dimer and ethylene oxide was 0.11 mass %.

(3) Purification by Distillation

After 0.66 g of maleic acid was added to the obtained reaction mixture, the mixture was transferred into a glass round-bottom flask of which capacity was 1.5 L. The flask was set in a vacuum distillation apparatus. While air was bubbled at a rate of 10 mL/min, hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.20 mass %, and a concentration of an addition reaction product of acrylic acid dimer and ethylene oxide was 0.005 mass %.

(4) Preservation Stability Test

In a glass screw bottle of which capacity was 50 mL, 30.0 g of the above hydroxyethyl acrylate was added. The screw bottle was covered and immersed into a thermostatic bath of 60° C. for preservation stability test. About 1 g of a sample was taken 90 days after the start of the test and analyzed by gas chromatography; as a result, a concentration of ethylene glycol diacrylate was 0.54 mass %.

Example 2: Production of Hydroxyethyl Acrylate (1) Analysis of Raw Material Acrylic Acid The acrylic acid which had been produced in the factory of the applicant of this application and stored in a tank was analyzed by gas chromatography. As a result, a concentration of acrylic acid dimer was 2.73 mass %.

(2) Esterification Reaction

The above raw material acrylic acid (658 g) produced by NIPPON SHOKUBAI CO., LTD., chromium acetate as a catalyst (2.62 g) and hydroquinone monomethyl ether as a polymerization inhibitor (1.44 g) were added into an autoclave of which capacity was 1.5 L, which was equipped with an agitator and which was made of SUS-316. After the gas phase in the autoclave was replaced by nitrogen gas, the temperature of the mixture was raised to 50° C. and the internal pressure was increased to 0.1 MPa in gauge pressure. Then, while the temperature of the mixture was maintained at 50° C., ethylene oxide (279.3 g out of 418.5 g, molar ratio relative to the pure acrylic acid was 1.070) produced by NIPPON SHOKUBAI CO., LTD. was added over about 60 minutes. Then, 139.2 g of ethylene oxide was added over about 120 minutes by changing the addition speed. After the addition of ethylene oxide, the reaction temperature was raised to 70° C. The reaction was carried out while a sample was taken with time and a concentration of unreacted acrylic acid was measured. When 3 hours passed after ethylene oxide was completely added and the concentration of unreacted acrylic acid in the whole reaction mixture became 0.10 mass %, the reaction was stopped by cooling the reaction mixture to 40° C.

The obtained reaction mixture was analyzed by gas chromatography. As a result, a concentration of ethylene glycol diacrylate was 0.20 mass %, and a concentration of an addition reaction product of acrylic acid dimer and ethylene oxide was 2.20 mass %.

(3) Purification by Distillation

After 0.66 g of maleic acid was added to the obtained reaction mixture, the mixture was transferred into a glass round-bottom flask of which capacity was 1.5 L. The flask was set in a vacuum distillation apparatus. While air was bubbled at a rate of 10 mL/min, hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.20 mass %, and a concentration of an addition reaction product of acrylic acid dimer and ethylene oxide was 0.10 mass %.

(4) Preservation Stability Test

In a glass screw bottle of which capacity was 50 mL, 30.0 g of the above hydroxyethyl acrylate was added. The screw bottle was covered and immersed into a thermostatic bath of 60° C. for preservation stability test. About 1 g of a sample was taken 90 days after the start of the test and analyzed by gas chromatography; as a result, a concentration of ethylene glycol diacrylate was 0.60 mass %.

Comparative Example 1: Production of Hydroxyethyl Acrylate (1) Analysis of Raw Material Acrylic Acid The acrylic acid which had been produced in the factory of the applicant of this application and stored in a tank was analyzed by gas chromatography. As a result, a concentration of acrylic acid dimer was 4.09 mass %.

(2) Esterification Reaction

The above raw material acrylic acid (658 g) produced by NIPPON SHOKUBAI CO., LTD., chromium acetate as a catalyst (2.62 g) and hydroquinone monomethyl ether as a polymerization inhibitor (1.44 g) were added into an autoclave of which capacity was 1.5 L, which was equipped with an agitator and which was made of SUS-316. After the gas phase in the autoclave was replaced by nitrogen gas, the temperature of the mixture was raised to 50° C. and the internal pressure was increased to 0.1 MPa in gauge pressure. Then, while the temperature of the mixture was maintained at 50° C., ethylene oxide (275.5 g out of 412.8 g, molar ratio relative to the pure acrylic acid was 1.070) produced by NIPPON SHOKUBAI CO., LTD. was added over about 60 minutes. Then, 137.3 g of ethylene oxide was added over about 120 minutes by changing the addition speed. After the addition of ethylene oxide, the reaction temperature was raised to 70° C. The reaction was carried out while a sample was taken with time and a concentration of unreacted acrylic acid was measured. When 3 hours passed after ethylene oxide was completely added and the concentration of unreacted acrylic acid in the whole reaction mixture became 0.10 mass %, the reaction was stopped by cooling the reaction mixture to 40° C.

The obtained reaction mixture was analyzed by gas chromatography. As a result, a concentration of ethylene glycol diacrylate was 0.20 mass %, and a concentration of an addition reaction product of acrylic acid dimer and ethylene oxide was 3.31 mass %.

(3) Purification by Distillation

After 0.66 g of maleic acid was added to the obtained reaction mixture, the mixture was transferred into a glass round-bottom flask of which capacity was 1.5 L. The flask was set in a vacuum distillation apparatus. While air was bubbled at a rate of 10 mL/min, hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.20 mass %, and a concentration of an addition reaction product of acrylic acid dimer and ethylene oxide was 0.15 mass %.

(4) Preservation Stability Test

In a glass screw bottle of which capacity was 50 mL, 30.0 g of the above hydroxyethyl acrylate was added. The screw bottle was covered and immersed into a thermostatic bath of 60° C. for preservation stability test. About 1 g of a sample was taken 90 days after the start of the test and analyzed by gas chromatography; as a result, a concentration of ethylene glycol diacrylate was 0.63 mass %.

Comparing the results of the preservation stability test of Examples 1 and 2 and Comparative Example 1, it was found that the higher the concentration of the reaction product of acrylic acid dimer and ethylene oxide was, the faster the increase rate of ethylene glycol diacrylate became. In addition, in comparison with Comparative Example 1, the generation of ethylene glycol diacrylate was inhibited by about 4.8 mass % in Example 2 and about 14.3 mass % in Example 1. Depending on such decrement, it can be expected that the turbidity and gelatinization of the produced hydroxyethyl acrylate during storage is inhibited, and the turbidity and undesired gelatinization of a reaction mixture is also inhibited when the produced hydroxyethyl acrylate is used to be polymerized.

From the above results, it is suggested that the concentration of the reaction product of acrylic acid dimer and ethylene oxide correlates with the increase rate of ethylene glycol diacrylate. Though the reason for the result is not necessarily clear, it is considered to be one of the reasons that the reaction product of acrylic acid dimer and ethylene oxide is decomposed to generate acrylic acid by heating and ethylene glycol diacrylate is formed from the generated acrylic acid.

Example 3: Production of Hydroxyethyl Acrylate (1) Analysis of Raw Material Acrylic Acid The acrylic acid which had been produced in the factory of the applicant of this application and stored in a tank was analyzed by gas chromatography. As a result, a concentration of acrylic acid dimer was 0.10 mass %.

(2) Esterification Reaction

The above raw material acrylic acid (420 g) produced by NIPPON SHOKUBAI CO., LTD., chromium acetate as a catalyst (2.10 g) and phenothiazine as a polymerization inhibitor (0.42 g) were added into an autoclave of which capacity was 1 L, which was equipped with an agitator and which was made of SUS-316. After the gas phase in the autoclave was replaced by nitrogen gas, the temperature of the reaction mixture was raised to 80° C. and the internal pressure was increased to 0.1 MPa in gauge pressure. Then, while the temperature of the mixture was maintained at 80° C., ethylene oxide (270 g, molar ratio relative to the pure acrylic acid was 1.053) produced by NIPPON SHOKUBAI CO., LTD. was added at the rate of 90 g/h over about 3 hours. After the addition of ethylene oxide, the reaction was carried out while the temperature was maintained at 80° C. and a sample was taken with time to measure a concentration of unreacted acrylic acid. When 2.2 hours passed after ethylene oxide was completely added and the concentration of unreacted acrylic acid in the whole reaction mixture became 0.10 mass %, the reaction was stopped by cooling the reaction mixture to 40° C.

The obtained reaction mixture was analyzed by gas chromatography. As a result, a concentration of ethylene glycol diacrylate was 0.40 mass %, and a concentration of an addition reaction product of acrylic acid dimer and ethylene oxide was 0.60 mass %.

(3) Purification by Distillation

After 0.53 g of maleic acid was added to the obtained reaction mixture, the mixture was transferred into a glass round-bottom flask of which capacity was 1 L. The flask was set in a vacuum distillation apparatus. While air was bubbled at a rate of 10 mL/min, hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.4 mass %, and a concentration of an addition reaction product of acrylic acid dimer and ethylene oxide was 0.027 mass %.

Example 4: Production of Hydroxyethyl Acrylate (1) Analysis of Raw Material Acrylic Acid The acrylic acid which had been produced in the factory of the applicant of this application and stored in a tank was analyzed by gas chromatography. As a result, a concentration of acrylic acid dimer was 0.90 mass %.

(2) Esterification Reaction

Esterification reaction was carried out in the same condition as the above-described Example 3(2) except that the above raw material acrylic acid produced by NIPPON SHOKUBAI CO., LTD. was used. However, the concentration of unreacted acrylic acid in the reaction mixture was not measured, and the reaction period from the completion of addition of ethylene oxide was set to be 2.2 hours similarly to the above-described Example 3 (2).

The obtained reaction mixture was analyzed by gas chromatography. As a result, a concentration of ethylene glycol diacrylate was 0.46 mass %, and a concentration of an addition reaction product of acrylic acid dimer and ethylene oxide was 1.23 mass % and it was demonstrated that the amount of an addition reaction product of acrylic acid dimer and ethylene oxide was increased.

(3) Purification by Distillation

Hydroxyethyl acrylate was distilled from the obtained reaction mixture under the same condition as the above-described Example 3 (3). A concentration of ethylene glycol diacrylate was 0.46 mass %, and a concentration of an addition reaction product of acrylic acid dimer and ethylene oxide was 0.058 mass %. As such a result, a concentration of an impurity was increased in comparison with the above-described Example 3; however, such an increment was little more than an amount which can be reduced by distillation.

Example 5: Production of Hydroxyethyl Acrylate (1) Analysis and Preparation of Raw Material Acrylic Acid The acrylic acid was stored in a tank at about 20° C. without increasing or decreasing the amount thereof for about 3 months after Example 3 was carried out, and then the acrylic acid was analyzed by gas chromatography. As a result, a concentration of acrylic acid dimer was 1.30 mass %.

The acrylic acid was mixed with acrylic acid of which concentration of acrylic acid dimer was 0.05 mass % and which was produced by NIPPON SHOKUBAI CO., LTD. so that the concentration of acrylic acid dimer was adjusted to be 0.20 mass %.

(2) Esterification Reaction

Esterification reaction was carried out in the same condition as the above-described Example 3(2) except that the above raw material acrylic acid was used. Similarly to the above-described Example 3(2), the concentration of unreacted acrylic acid became 0.10 mass % 2.2 hours after ethylene oxide was completely supplied.

The obtained reaction mixture was analyzed by gas chromatography. As a result, a concentration of ethylene glycol diacrylate was 0.40 mass %, and a concentration of an addition reaction product of acrylic acid dimer and ethylene oxide was 0.68 mass %.

(3) Purification by Distillation

Hydroxyethyl acrylate was distilled from the obtained reaction mixture under the same condition as the above-described Example 3 (3). A concentration of ethylene glycol diacrylate was 0.40 mass %, and a concentration of an addition reaction product of acrylic acid dimer and ethylene oxide was 0.031 mass %.

Example 6: Production of Hydroxyethyl Acrylate (1) Esterification Reaction

Esterification reaction was carried out in the same condition as the above-described Example 3(2) except that the acrylic acid which was stored for about 3 months similarly to the above-described Example 5(1) was used as it was. However, the concentration of unreacted acrylic acid in the reaction mixture was not measured, and the reaction period from the completion of addition of ethylene oxide was set to be 2.2 hours similarly to the above-described Example 3 (2).

The obtained reaction mixture was analyzed by gas chromatography. As a result, a concentration of ethylene glycol diacrylate was 0.46 mass %, and a concentration of an addition reaction product of acrylic acid dimer and ethylene oxide was 1.55 mass % and it was demonstrated that the amount of an addition reaction product of acrylic acid dimer and ethylene oxide was increased.

(2) Purification by Distillation

Hydroxyethyl acrylate was distilled from the obtained reaction mixture under the same condition as the above-described Example 3 (3). A concentration of ethylene glycol diacrylate was 0.46 mass %, and a concentration of an addition reaction product of acrylic acid dimer and ethylene oxide was 0.073 mass %. As such a result, a concentration of an impurity was increased in comparison with the above-described Example 5; however, such an increment was little more than an amount which can be reduced by distillation.

Example 7: Production of Hydroxyethyl Acrylate (1) Esterification Reaction

As raw material acrylic acid, acrylic acid of which concentration of acrylic acid dimer was 0.70 mass % and which was produced by NIPPON SHOKUBAI CO., LTD. was used. The acrylic acid (420 kg), chromium acetate as a catalyst (2.10 kg) and phenothiazine as a polymerization inhibitor (0.42 kg) were added into an autoclave of which capacity was 1 m$^3$, which was equipped with an agitator and which was made of SUS-316. After the gas phase in the autoclave was replaced by nitrogen gas, the temperature of the reaction mixture was raised to 80° C. and the internal pressure was increased to 0.1 MPa in gauge pressure. Then, while the temperature of the mixture was maintained at 80° C., ethylene oxide (270 kg, molar ratio relative to the pure acrylic acid was 1.059) produced by NIPPON SHOKUBAI CO., LTD. was added at a rate of 90 kg/h over about 3 hours. The reaction was carried out while the temperature was maintained at 80° C. and a sample was taken with time to measure a concentration of unreacted acrylic acid. When the concentration of unreacted acrylic acid became 0.10 mass % 2.2 hours after ethylene oxide was completely added, the reaction was stopped by cooling the reaction mixture to 40° C.

The obtained reaction mixture was analyzed by gas chromatography. As a result, a concentration of ethylene glycol diacrylate was 0.46 mass %, and a concentration of an addition reaction product of acrylic acid dimer and ethylene oxide was 1.07 mass %.

(2) Purification by Distillation

After 0.53 kg of maleic acid was added to the obtained reaction mixture, the mixture was transferred into a distillation apparatus of which capacity was 1 m$^3$. Hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.46 mass %, and a concentration of an addition reaction product of acrylic acid dimer and ethylene oxide was 0.049 mass %.

Example 8: Production of Hydroxyethyl Acrylate (1) Esterification Reaction

A use amount of ethylene oxide was determined so that the molar ratio of alkylene oxide relative to acrylic acid was adjusted to be the same 1.053 as the case of Example 3(2). The molar ratio is calculated by the following formula. The molar ratio in the above-described Example 7 was 1.059.

Molar ratio of AO/AA=(mass of AO/molecular weight of AO)/({mass of raw material AA×[(100−concentration of AA dimer)/100]}/molecular weight of AA)

wherein AO represents alkylene oxide, AA represents acrylic acid, molar ratio of AO/AA represents the molar ratio of alkylene oxide relative to acrylic acid, units of mass of AO and mass of AA are g, and a unit of concentration of AA dimer is mass %.

As raw material acrylic acid, acrylic acid which was used in Example 7 was used. The acrylic acid (420 kg) produced by NIPPON SHOKUBAI CO., LTD., chromium acetate as a catalyst (2.10 kg) and phenothiazine as a polymerization inhibitor (0.42 kg) were added into an autoclave of which capacity was 1 m$^3$, which was equipped with an agitator and which was made of SUS-316. After the gas phase in the autoclave was replaced by nitrogen gas, the temperature of the reaction mixture was raised to 80° C. and the internal pressure was increased to 0.1 MPa in gauge pressure. Then, while the temperature of the reaction mixture was maintained at 80° C., ethylene oxide (268 kg, molar ratio relative to the pure acrylic acid was 1.053) produced by NIPPON SHOKUBAI CO., LTD. was added at the rate of 89 kg/h over about 3 hours. The reaction was carried out while the temperature was maintained at 80° C. and a sample was taken with time to measure a concentration of unreacted acrylic acid. When the concentration of unreacted acrylic acid became 0.10 mass % 2.2 hours after ethylene oxide was completely added, the reaction was stopped by cooling the reaction mixture to 40° C.

The obtained reaction mixture was analyzed by gas chromatography. As a result, a concentration of ethylene glycol diacrylate was 0.40 mass %, and a concentration of an addition reaction product of acrylic acid dimer and ethylene oxide was 1.08 mass %.

(2) Purification by Distillation

After 0.53 kg of maleic acid was added to the obtained reaction mixture, the mixture was transferred into a distillation apparatus of which capacity was 1 m³. Hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.40 mass %, and a concentration of an addition reaction product of acrylic acid dimer and ethylene oxide was 0.049 mass %.

Comparing the results of Example 7 and Example 8, it was demonstrated that even if a concentration of acrylic acid dimer in acrylic acid used as raw material is the same, a generation amount of ethylene glycol diacrylate and a contamination amount of ethylene glycol diacrylate in the target compound can be decreased by adjusting the use amount of ethylene oxide depending on concentration of acrylic acid dimer in the acrylic acid.

Example 9: Production of Hydroxyethyl Acrylate (1) Esterification Reaction

As raw material acrylic acid, acrylic acid which was used in Example 3 was used. The acrylic acid (272 kg out of the total use amount of 816 kg), chromium acetate as a catalyst (4.90 kg) and phenothiazine as a polymerization inhibitor (0.82 kg) were added into a reactor of which capacity was 2 m³ and which was equipped with an agitator. After the gas phase in the reactor was replaced by nitrogen gas, the temperature of the reaction mixture was raised to 85° C. and the internal pressure was increased to 0.1 MPa in gauge pressure. Then, ethylene oxide (210.2 kg) was added at a rate of 262.7 kg/h over 0.8 hours. Next, while the temperature was maintained at 85° C., 544 kg of acrylic acid was added at a rate of 453.3 kg/h over 1.2 hours and 314.8 kg of ethylene oxide was added at a rate of 262.7 kg/h over 1.2 hours. The reaction was continued until the concentration of unreacted acrylic acid became 0.10 mass % while the temperature was maintained at 85° C. after the addition of acrylic acid and ethylene oxide. After the concentration of unreacted acrylic acid became 0.10 mass % by continuing the reaction for 2.0 hours, the reaction mixture was cooled to 40° C. The obtained reaction mixture was analyzed by gas chromatography. As a result, a concentration of ethylene glycol diacrylate was 0.24 mass %, and a concentration of an addition reaction product of acrylic acid dimer and ethylene oxide was 0.27 mass %.

(2) Purification by Distillation

After 1.24 kg of maleic acid was added to the obtained reaction mixture, the mixture was transferred into a distillation apparatus of which capacity was 2 m³. Hydroxyethyl acrylate was distilled under a pressure of 2 to 10 hPa at an inside temperature of 60 to 100° C. for 3 hours until a distillate ratio became 90%.

The obtained hydroxyethyl acrylate was analyzed by gas chromatography; as a result, a concentration of ethylene glycol diacrylate was 0.24 mass %, and a concentration of an addition reaction product of acrylic acid dimer and ethylene oxide was 0.012 mass %.

Example 10: Production of Hydroxyethyl Acrylate (1) Esterification Reaction

The acrylic acid was stored in a tank at about 20° C. without increasing or decreasing the amount thereof for about 3 months after Example 9 was carried out, and then the acrylic acid was analyzed by gas chromatography. As a result, a concentration of acrylic acid dimer was 1.3 mass %.

Esterification reaction was carried out in the same condition of the above-described Example 9(1) except that the above acrylic acid was used. However, the concentration of unreacted acrylic acid in the reaction mixture was not measured, and the reaction period from the completion of addition of ethylene oxide was set to be 2.0 hours similarly to the above-described Example 9(1).

The obtained reaction mixture was analyzed by gas chromatography. As a result, a concentration of ethylene glycol diacrylate was 0.27 mass %, and a concentration of an addition reaction product of acrylic acid dimer and ethylene oxide was 1.22 mass %.

(2) Purification by Distillation

Hydroxyethyl acrylate was distilled from the obtained reaction mixture under the same condition as the above-described Example 9 (2). A concentration of ethylene glycol diacrylate was 0.27 mass %, and a concentration of an addition reaction product of acrylic acid dimer and ethylene oxide was 0.056 mass %. As such a result, a concentration of an impurity was increased in comparison with the above-described Example 9; however, such an increment was little more than an amount which can be reduced by distillation.

The invention claimed is:

1. A method for producing a hydroxyalkyl acrylate, comprising the step of reacting a raw material acrylic acid comprising acrylic acid and acrylic acid dimer with an alkylene oxide in the presence of a catalyst,
wherein an amount of acrylic acid dimer in the raw material acrylic acid is less than or equal to 3.00 mass %, and
wherein a molar ratio of the alkylene oxide relative to the acrylic acid is adjusted to be more than or equal to 1.010 and less than or equal to 1.055, and the molar ratio is calculated by the following formula:

molar ratio of AO/AA=(mass of AO/molecular weight of AO)/({mass of raw material AA×[(100−concentration of AA dimer)/100]}/molecular weight of AA), wherein AO represents alkylene oxide, AA represents acrylic acid, molar ratio of AO/AA represents the molar ratio of the alkylene oxide relative to the acrylic acid, units of mass of AO and mass of AA are g, and a unit of concentration of AA dimer is mass %.

2. The method according to claim 1, further comprising the step of adjusting the amount of acrylic acid dimer in the raw material acrylic acid to be less than or equal to 3.00 mass % when the amount of the acrylic acid dimer is more than 3.00 mass %.

3. The method according to claim 1, wherein an initial charged amount of the raw material acrylic acid is adjusted to be less than or equal to 90 mass % of the whole use amount, and after all of or a part of the alkylene oxide is supplied, the rest of the raw material acrylic acid is supplied.

4. The method according to claim 1, wherein ethylene oxide or propylene oxide is used as the alkylene oxide.

5. The method according to claim 2, wherein an initial charged amount of the raw material acrylic acid is adjusted to be less than or equal to 90 mass % of the whole use amount, and after all or a part of the alkylene oxide is supplied, the rest of the raw material acrylic acid is supplied.

6. The method according to claim 2, wherein ethylene oxide or propylene oxide is used as the alkylene oxide.

7. The method according to claim 3, wherein ethylene oxide or propylene oxide is used as the alkylene oxide.

* * * * *